United States Patent [19]

Pastrick

[11] 4,246,662
[45] Jan. 27, 1981

[54] PROSTHETIC JOINT

[75] Inventor: Danny L. Pastrick, Warsaw, Ind.

[73] Assignee: Zimmer USA, Inc., Warsaw, Ind.

[21] Appl. No.: 46,297

[22] Filed: Jun. 7, 1979

[51] Int. Cl.³ .............................................. A61F 1/03
[52] U.S. Cl. .................................... 3/1.91; 128/92 C
[58] Field of Search .............................. 3/1.91, 1.911; 128/92 C

[56] References Cited

U.S. PATENT DOCUMENTS 3,739,403  6/1973  Nicolle .................................... 3/1.91
3,875,594  4/1975  Swanson ................................. 3/1.91

Primary Examiner—Clifford D. Crowder

Attorney, Agent, or Firm—Richard H. Brink

[57] ABSTRACT

A prosthetic joint for replacement of bone joints having a one-piece body of flexible physiologically inert material. The body has an enlarged central portion with two stem portions extending oppositely from the central portion for insertion into the medullary canal of bone. The central portion of the body has a height equal to or greater than its width and a slot extending substantially through the enlarged central portion from the distal end of the dorsal surface of the central portion toward the proximal end of the volar surface of the central portion forming a hinge at the volar surface. The hinge is offset from the center of said central portion toward the proximal end of the central portion.

5 Claims, 8 Drawing Figures

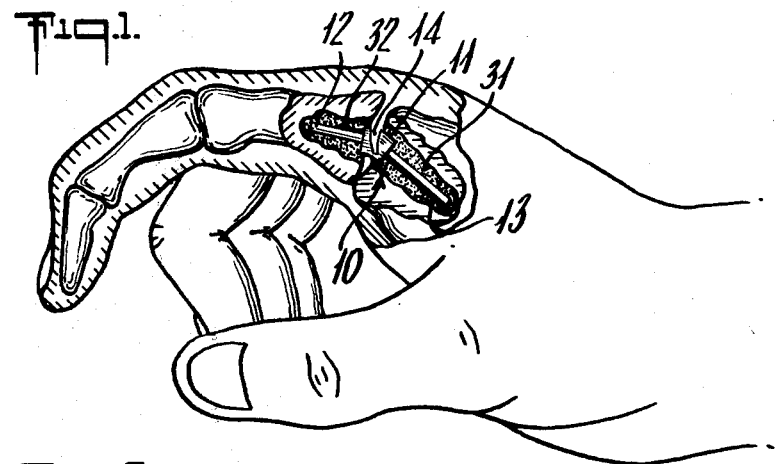
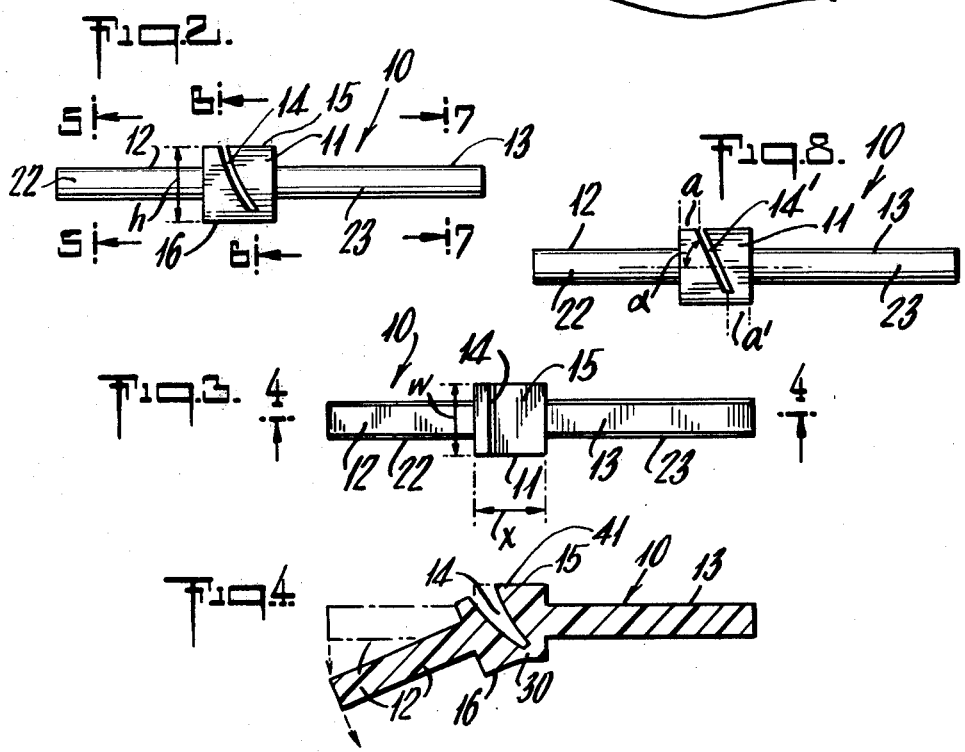
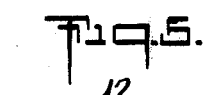
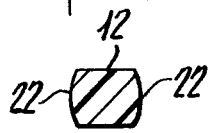
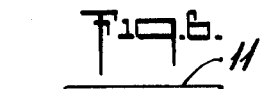
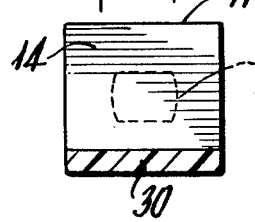
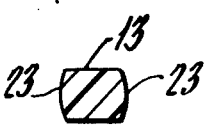

PROSTHETIC JOINT

BACKGROUND OF THE INVENTION

This invention relates to orthopaedic appliances. More particularly, this invention relates to joint prostheses and especially to prosthetic devices for the replacement of metacarpal joints.

Prosthetic devices for the replacement of metacarpal joints damaged by rheumatoid arthritis, infection or trauma are well known. Typical examples of such devices are described in U.S. Pat. Nos. 3,462,765; 3,875,579; 3,681,786; 3,593,342 and 3,739,403.

While some of the foregoing prosthetic joints have attained some degree of commercial success, they have certain disadvantages. Common problems are "swan neck" deformity resulting in breakage of the prosthesis at the stem/hinge interface, tissue ingrowth in the hinge area, and bending of the prosthesis outside the joint area. Accordingly, it is an object of this invention to provide a joint prosthesis not having the foregoing disadvantages.

The joint prosthesis of this invention is an improvement over known metacarpal joint prostheses. The central portion more evenly distributes the compressive forces found in a normal metacarpal joint and due to its height being equal to or greater than its width the opportunity of "swan neck" deformity of the prosthesis is therefore reduced, as well as the incidence of breakage at the stem/hinge interface. The angled or curved slot in the central portion extending from the more distal end of the top portion in the palmar aspect volarly toward the proximal end of the bottom portion allows for proper positioning of the center of motion in the proximal and volar aspect of the hinge which conforms closely to normal anatomy, as well as creating a "ledge" which inhibits tissue ingrowth into the hinge area. The arrangement of the slot also acts as a restraint to allow bending in only one direction. The stems are also designed to reduce rotation and allow for orientation of the prosthesis.

SUMMARY OF THE INVENTION

Briefly stated, this invention relates to a joint prosthesis particularly adapted for replacement of the metacarpophalangeal joint (knuckle) and proximal interphalangeal joint of the phalanges of the hand. The prosthesis includes a one-piece body of flexible inert material. The prosthesis has a central portion between two intramedullary stems with a slot extending substantially through the central portion from the dorsal surface to approximately the volar surface to create a hinge with the volar surface. The slot extends from approximately the distal end of the dorsal surface toward the proximal end of the volar surface. The central portion also has a height equal to or greater than its width.

BRIEF DESCRIPTION OF THE DRAWINGS

FIG. 1 is a partial cross-section of a metacarpal joint of a human hand that has been implanted with a joint prosthesis constructed in compliance with the present invention;

FIG. 2 is a side elevational view of the prosthesis of this invention;

FIG. 3 is a top plan view of the prosthesis;

FIG. 4 is a cross-sectional view taken along lines 4—4 of FIG. 3 showing the joint prosthesis in a flexed position;

FIG. 5 is an enlarged cross-sectional view of the distal stem taken along the lines 5—5 of FIG. 2;

FIG. 6 is an enlarged cross-sectional view of the central portion taken along lines 6—6 of FIG. 2;

FIG. 7 is an enlarged cross-sectional view of the proximal end taken along lines 7—7 of FIG. 2; and FIG. 8 is a side elevational view of another embodiment of the prosthesis of this invention.

DETAILED DESCRIPTION OF THE INVENTION

FIG. 1 illustrates the prosthesis of this invention 10 in place in the medullary canals 31 and 32 of a metacarpal bone of the hand. The prosthesis is implanted in a metacarpal joint of the hand by a procedure which generally consists of partial surgical removal of the metacarpal joint, reaming of the medullary canals 31 and 32 and introducing the prosthetic joint in place in the medullary canals.

The joint prosthesis 10 as shown in FIGS. 2-8 is a one-piece body of flexible physiologically inert material such as silicone rubber or polyethylene and is preferably produced by molding. The joint prosthesis can be molded in one piece or in two or more pieces, for example the stems and central portion can be molded separately and cemented together with an adhesive such as SILASTIC Medical Adhesive, Silicon Type A, marketed by Dow Corning.

The prosthesis includes an enlarged central section 11 with two stem portions 12 and 13 extending oppositely from the central section. The proximal stem 13 is slightly longer than the distal stem 12. Preferably, the stems are semi-rectangular with curved sidewalls 22 and 23 allowing them to conform to the intramedullary canal of the bone. The semi-rectangular shape of the stems tends to reduce rotation of the prosthesis after it is implanted and allows for better orientation of the prosthesis during surgical implantation.

The enlarged central section 11 as shown in FIGS. 1 and 4 is of a height h equal to or greater than its width w. The width and height requirements greatly strengthen the central section and substantially reduce the occurrence of "swan neck" deformity of the prosthesis, as well as the incidence of breakage at the stem/central section interface.

A slot 14 extends from the dorsal surface 15 substantially to the volar surface 16 of the central section. The slot begins at the distal end of the dorsal surface and extends toward the proximal end of the volar surface, preferably at an angle $\alpha$ of about 55° to 60° measured clockwise from a plane parallel to the volar surface when the prosthesis is in a straight extended position. The angle $\alpha$ is shown in FIG. 8. In FIG. 2 the slot is shown as slightly arcuate having a radius of about 30°. In FIG. 8 another embodiment of the invention is shown in which the slot 14 is straight. The distances a and a' are preferably equal and each is equal to about 20-25% of the length x of the central section as shown in FIGS. 3 and 8.

As shown in FIG. 4 a hinge 30 is produced by slot 14 near the volar surface of the central section which is offset toward the proximal end of the central section.

This offset allows as shown in FIG. 1 for proper positioning of the center of motion toward the proximal end of the central section in the proximal and volar aspect of the hinge to approximate that of the natural joint. The location of the slot in the dorsal surface creates a ledge 41 which inhibits tissue ingrowth into the hinge area 14 and the design of the slot and hinge acts as a restraint to allow bending or flexing of the prosthesis in only one direction.

Thus, it is apparent that the prosthesis of this invention has overcome various disadvantages of known metacarpal joint prostheses and represents a significant advancement in the art.

While this invention has been described and exemplified in terms of its preferred embodiment, those skilled in the art will appreciate that modifications can be made without departing from the spirit and scope of this invention.

I claim:

1. A prosthetic joint for replacement of bone joints comprising a one-piece body of flexible physiologically inert material, said body having an enlarged central portion and outwardly directed proximal and distal stem portions each adapted to be inserted into a medullary canal of a bone of said joint, said central portion having a height equal to or greater than its width and a slot extending substantially through said central portion from the distal end of the dorsal surface of said central portion toward the proximal end of the volar surface of said central portion forming a hinge near the volar surface which is offset from the center of said central portion toward the proximal end of said central portion.

2. The prosthetic joint of claim 1, wherein said slot is at an angle of about 55° to 60° measured clockwise from a plane parallel to the volar surface when the prosthesis is in a straight extended position.

3. The prosthetic joint of claim 1 wherein said body is silicone rubber.

4. The prosthetic joint of claim 1 wherein said slot is straight.

5. The prosthetic joint of claim 1 wherein said slot is arcuate.